(12) United States Patent
Najafi et al.

(10) Patent No.: US 8,979,665 B1
(45) Date of Patent: Mar. 17, 2015

(54) PROVIDING MOTION FEEDBACK BASED ON USER CENTER OF MASS

(76) Inventors: Bijan Najafi, Vernon Hills, IL (US); James Stanley Wrobel, Grayslake, IL (US); Ali-Reza Boloori, Los Angeles, CA (US)

(*) Notice: Subject to any disclaimer, the term of this patent is extended or adjusted under 35 U.S.C. 154(b) by 574 days.

(21) Appl. No.: 13/053,147

(22) Filed: Mar. 21, 2011

Related U.S. Application Data

(60) Provisional application No. 61/316,023, filed on Mar. 22, 2010.

(51) Int. Cl.
*A63B 69/00* (2006.01)

(52) U.S. Cl.
USPC .......................................... 473/269; 473/266

(58) Field of Classification Search
CPC ............... A63B 2024/00; A63B 2024/0003; A63B 2024/0006; A63B 2024/0012; A63B 2024/0015; A63B 69/3667; A63B 69/3608
USPC .................................................. 473/266, 269
See application file for complete search history.

(56) References Cited

U.S. PATENT DOCUMENTS

| | | | |
|---|---|---|---|
| 3,702,999 A | 11/1972 | Gradisar | |
| 5,373,651 A | 12/1994 | Wood | |
| 5,642,096 A | 6/1997 | Leyerer et al. | |
| 5,697,791 A * | 12/1997 | Nashner et al. | 434/247 |
| 5,907,819 A * | 5/1999 | Johnson | 702/152 |
| 6,119,516 A | 9/2000 | Hock | |
| 6,201,476 B1 | 3/2001 | Depeursinge et al. | |
| 6,433,690 B2 | 8/2002 | Petelenz et al. | |
| 6,730,024 B2 | 5/2004 | Freyre et al. | |
| 6,890,285 B2 | 5/2005 | Rahman et al. | |
| 6,926,667 B2 | 8/2005 | Khouri | |
| 6,997,882 B1 | 2/2006 | Parker et al. | |
| 7,141,026 B2 | 11/2006 | Aminian et al. | |
| 7,166,063 B2 | 1/2007 | Rahman et al. | |
| 7,334,472 B2 | 2/2008 | Seo et al. | |

(Continued)

FOREIGN PATENT DOCUMENTS

| | | |
|---|---|---|
| EP | 1195139 A1 | 4/2002 |
| WO | WO 03/065891 A2 | 8/2003 |

OTHER PUBLICATIONS

U.S. Appl. No. 13/531,313, filed Jun. 22, 2012, Najafi et al.

(Continued)

*Primary Examiner* — Lawrence Galka
(74) *Attorney, Agent, or Firm* — Knobbe, Martens, Olson & Bear, LLP

(57) ABSTRACT

The present disclosure is directed to a body-worn sensor-based system for evaluating the biomechanics and the motor adaptation characteristics of postural control during a sport activity such as a golf swing. Various embodiments use sensors such as accelerometers, gyroscopes, and magnetometers to measure the three-dimensional motion of ankle and hip joints. In several embodiments, additional sensors attached to other body segments are used to improve the accuracy of the data or detect particular instants during the swing (e.g., top of back swing, instant of the maximum speed of arm, and instant of ball impact). In a golf embodiment, the system combines the measured data in conjunction with a biomechanical model of the human body to: (1) estimate the two-dimensional sway of the golfer's center of mass; (2) quantify and evaluate the golfer's balance via his/her postural compensatory strategy; and (3) provide visual feedback to the golfer for improving dynamic postural control.

27 Claims, 15 Drawing Sheets

(56) References Cited

U.S. PATENT DOCUMENTS

| | | | |
|---|---|---|---|
| 7,620,450 B2 | 11/2009 | Kim et al. | |
| 7,627,450 B2 | 12/2009 | Lee et al. | |
| 7,632,216 B2 | 12/2009 | Rahman et al. | |
| 7,634,379 B2 | 12/2009 | Noble | |
| 7,640,134 B2 | 12/2009 | Park et al. | |
| 7,701,354 B2 | 4/2010 | Chung | |
| 7,725,289 B2 | 5/2010 | Nagashima et al. | |
| 7,747,409 B2 | 6/2010 | Ladetto et al. | |
| 7,771,371 B2 | 8/2010 | Avni | |
| 7,857,771 B2 | 12/2010 | Alwan et al. | |
| 7,962,308 B2 | 6/2011 | Makino | |
| 7,983,872 B2 | 7/2011 | Makino et al. | |
| 8,007,450 B2 | 8/2011 | Williams | |
| 8,025,632 B2 | 9/2011 | Einarsson | |
| 8,206,325 B1 | 6/2012 | Najafi et al. | |
| 8,212,650 B2 | 7/2012 | Tsern et al. | |
| 8,242,879 B2 | 8/2012 | Haynes et al. | |
| 8,384,551 B2 | 2/2013 | Ross et al. | |
| 8,388,553 B2 | 3/2013 | James et al. | |
| 2003/0065409 A1 | 4/2003 | Raeth et al. | |
| 2003/0139692 A1 | 7/2003 | Barrey et al. | |
| 2004/0015103 A1 | 1/2004 | Aminian et al. | |
| 2005/0043660 A1 | 2/2005 | Stark et al. | |
| 2005/0165336 A1 | 7/2005 | Rahman et al. | |
| 2006/0166157 A1 | 7/2006 | Rahman et al. | |
| 2006/0270949 A1 | 11/2006 | Mathie et al. | |
| 2007/0149359 A1 | 6/2007 | Rahman et al. | |
| 2007/0270214 A1* | 11/2007 | Bentley | 463/30 |
| 2007/0293781 A1 | 12/2007 | Sims et al. | |
| 2008/0091762 A1 | 4/2008 | Neuhauser et al. | |
| 2008/0281555 A1 | 11/2008 | Godin et al. | |
| 2008/0281636 A1 | 11/2008 | Jung et al. | |
| 2008/0318683 A1 | 12/2008 | Rofougaran et al. | |
| 2009/0002152 A1 | 1/2009 | Chung | |
| 2009/0024065 A1 | 1/2009 | Einarsson | |
| 2009/0055223 A1 | 2/2009 | Jung et al. | |
| 2009/0058660 A1 | 3/2009 | Torch | |
| 2009/0069724 A1 | 3/2009 | Otto et al. | |
| 2009/0076345 A1 | 3/2009 | Manicka et al. | |
| 2009/0099495 A1 | 4/2009 | Campos et al. | |
| 2009/0192414 A1 | 7/2009 | Yasuhara | |
| 2009/0234249 A1 | 9/2009 | Randolph | |
| 2009/0292194 A1 | 11/2009 | Libbus et al. | |
| 2010/0121227 A1* | 5/2010 | Stirling et al. | 600/595 |
| 2010/0286571 A1 | 11/2010 | Allum et al. | |
| 2010/0324455 A1 | 12/2010 | Rangel et al. | |
| 2011/0115629 A1 | 5/2011 | Holler et al. | |
| 2012/0184878 A1 | 7/2012 | Najafi et al. | |

OTHER PUBLICATIONS

U.S. Appl. No. 13/723,040, filed Dec. 20, 2012, Najafi et al.
American Diabetes Association, Apr. 7-8, 1999, Boston, Massachusetts, "Consensus development conference in diabetic foot wound care", Diabetes Care 22.8:1354 (Aug. 1999).
Aminian et al., "Spatio-temporal parameters of gait measured by an ambulatory system using miniature gyroscopes," *Journal of Biomechanics*, vol. 35:689-699 (2002).
Aminian et al., "Temporal feature estimation during walking using miniature accelerometers: an analysis of gait improvement after hip arthroplasty," *Medical & Biological Engineering & Computing*, vol. 37:686-691 (1999).
Armstrong et al., "Activity patterns of patients with diabetic foot ulceration", Diabetes Care, vol. 26(9):2595-2597 (2003).
Armstrong et al., "Continuous activity monitoring in persons a high risk for diabetes-related lower-extremity amputation", Journal of the American Podiatric Medical Association, vol. 91:451-455 (2001).
Armstrong et al., "Evaluation of removable and irremovable cast walkers in the healing of diabetic foot wounds: a randomized controlled trial", Diabetes Care, vol. 28:551-4 (2005).
Armstrong et al., "Variability in activity may precede diabetic foot ulceration", Diabetes Care, vol. 27(8):3028-3029 (2004).
B. Najafi, K. Aminian, F. Loew, Y. Blanc, and P. A. Robert, "Measurement of standsit and sit-stand transitions using a miniature gyroscope and its application in fall risk evaluation in the elderly," *Ieee Transactions on Biomedical Engineering*, vol. 49:843-851 (2002).
Bohannon et al., "Walking speed: reference values and correlates for older adults," *J Orthop Sports Phys Ther*, vol. 24:86-90 (1996).
Brand, Paul W. "The diabetic foot", Diabetes Mellitus, Theory and Practice, $3^{rd}$ Ed., Ellenberg M. Rifkin H., Ed. New York: Medical Examination Publishing, 1983, pp. 803-828.
Coleman et al., "The total contact cast, a therapy for plantar ulceration on insensitive feet", J.Am. Podiatr. Med. Assoc., vol. 74:548-552 (1984).
Cummings et al., "Forgetting falls. The limited accuracy of recall of falls in the elderly," *J Am Geriatr Soc*, vol. 36:613-6 (1988).
Doughty et al., "The design of a practical and reliable fall detector for community and institutional telecare," *J Telemed Telecare*, vol. 6 Suppl 1:S150-4 (2000).
Helm et al., "Total contact casting in diabetic patients with neuropathic foot ulcerations", Arch. Phys. Med. Rehabil., vol. 65:691-693 (1984).
Lavery et al., "Reducing dynamic foot pressures in high-risk diabetic subjects with foot ulcerations", Diabetes Care, vol. 19(8):818-821 (1996).
Lindemann et al., "Evaluation of a fall detector based on accelerometers: a pilot study," *Med Biol Eng Comput*, vol. 43:548-51 (2005).
Mizell, "Using gravity to estimate accelerometer orientation", Proceedings of the Seventh IEEE International Symposium on Wearable Computers, Computer Society (2003).
Najafi et al., "Ambulatory system for human motion analysis using a kinematic sensor: Monitoring of daily physical activity in the elderly," *Ieee Transactions on Biomedical Engineering*, vol. 50:711-723 (2003).
Najafi et al., "A novel ambulatory device for continuous 24-H monitoring of physical activity in daily life", North American Congress on Biomechanics (NACOB), Michigan, 2008.
Noury et al., "A smart sensor based on rules and its evaluation in daily routines," presented at 25th Annual International Conference of the IEEE Eng. Med. Biol. Society (2003).
Oliver et al., "Development and evaluation of evidence based risk assessment tool (STRATIFY) to predict which elderly inpatients will fall: case-control and cohort studies," *Bmj*, vol. 315:1049-53 (1997).
Pecoraro et al., "Pathways to diabetic limb amputation", Diabetes Care, vol. 13(5):513-521 (1990).
Sinacore et al., "Diabetic plantar ulcers treated by total contact casting", Phys. Ther. vol. 67:1543-1547 (1987).
Tinetti et al., "Fall risk index for elderly patients based on number of chronic disabilities," *Am J Med*, vol. 80: 429-34 (1986).
Walker et al., "Chronic diabetic neuropathic foot ulcerations and total contact casting: healing effectiveness and outcome predictability", Arch. Phys. Med. Rehabil., vol. 66:574 (1985).
Wu et al., "The pivotal role of offloading in the management of neuropathic foot ulceration", Curr. Diab. Rep. vol. 5:423-9 (2005).
Wu et al., "Use of pressure offloading devices in diabetic foot ulcers", Diabetes Care, vol. 31(11):2118-2119, (2008).

\* cited by examiner

PROVIDING MOTION FEEDBACK BASED ON USER CENTER OF MASS

CROSS-REFERENCE TO RELATED APPLICATIONS

This application claims priority to U.S. Provisional Patent Application No. 61/316,023, filed on Mar. 22, 2010, entitled "Sensor-Based System For Evaluating and Enhancing Postural Control and Balance in Golf," the entire contents of which are hereby incorporated herein by reference. All publications and patent applications mentioned in this specification are herein incorporated by reference in their entirety to the same extent as if each individual publication or patent application was specifically and individually indicated to be incorporated by reference.

BACKGROUND

1. Technical Field

Embodiments of the present invention relate to sensor-based systems and methods for evaluating and enhancing postural control and balance in sports activities.

2. Description of the Related Art

The golf swing is a complex movement, involving the whole body. To better understand how to improve the golf swing, researchers have studied the biomechanics of the golf swing. A key challenge in assessing the performance and effectiveness of a golf swing is finding a reliable metric value that is measurable in the field and that allows for identifying an ideal or near-ideal swing.

While many measures have been identified as possible indicators of the quality of the swing, novice and experienced golfers alike have difficulty in using them to improve their golf swing. Most studies have investigated the factors related to the angular velocity of the club head, which directly influences the distance the ball travels after impact with the club. Some studies have suggested that in an optimal swing, the golfer should 1) produce maximal ground reaction force (GRF) during the swing; and 2) gradually shift his body-weight from the back foot at the top of the backswing to the front foot during the downswing. Focusing on improving these two components can help players improve the golf ball's travel distance.

SUMMARY

The present disclosure is directed to helping players improve their golf swing. In one embodiment, a computing system (also termed a "postural and balance evaluation system") is configured to receive data collected from one or more sensors for measuring a player's body position and movement. The computing system may be adapted to receive such sensor data locally via a physical or wireless link, or remotely via a network (e.g., data collected remotely by sensors coupled with another computing system such as a mobile smartphone). In one embodiment, the computing system estimates the time points at which the maximum speed of the arm during an actual swing occurs. Using these time points, the computing system next estimates the position of the center of mass (COM) in the medial-lateral (M-L) (side-to-side) and the anterior-posterior (A-P) (front-to-bank) planes and provides the player with feedback on these positions. The computing system may additionally provide instructions to the player as to how to improve his or her swing. The instructions may be presented via a user interface displayed to the player. In one embodiment, to encourage improved performance from the player, several visual and auditory feedbacks may be provided (e.g., "exploding" the target on the screen when the speed of down swing is appropriate and/or when the position of COM in the current trial is closer to the ideal target when compared to a previous attempt.)

In one embodiment, to improve the effect of learning as a function of swing speed, the computing system may normalize these positions by the value of maximum speed of the arm during swing. One embodiment divides the COM position value by the value of arm speed. The normalization helps improve the effect of learning as a function of swing speed as follows. For very slow arm movements, the user's COM does not typically change because very slow arm movements do not destabilize the user's balance. In the extreme case, if there is little or no arm movement, the user may be in a perfectly stable position. Thus, a user may simply improve his/her outcome (reducing a difference between the ideal COM position and a COM position during the swing) by reducing his/her arm speed. However, since a reduced arm speed likely leads to worse overall performance (reduced ball distance), embodiments of the invention weigh (normalize) the amount of COM deviation by the maximum arm speed. This encourages the users to maximize arm speed while trying to reduce the area of COM sway, which helps users improve their postural control during challenging conditions in which the swing speed should be as high as possible to increase the distance of the golf shot. The computing system may be further configured to help users focus on the optimal placement of their COM in the M-L and A-P planes by multiplying the M-L and or the A-P COM position by a constant value.

In one embodiment, the visual feedback provided by the computing system could also help a player improve his or her balance (i.e., the position of COM) during particular instants of swing. The computing system is configured to provide feedback during particular instants that have been determined to correlate to improved performance, including, for example, at the top of the downswing, at the maximum speed of arm motion, and at impact (when the golf club meets the ball).

BRIEF DESCRIPTION OF THE DRAWINGS

Certain embodiments of the invention will now be described with reference to the drawings summarized below. These drawings and the associated description are provided to illustrate various embodiments of the invention, and not to limit the scope of the invention.

DETAILED DESCRIPTION OF CERTAIN EMBODIMENTS

Figure 1:
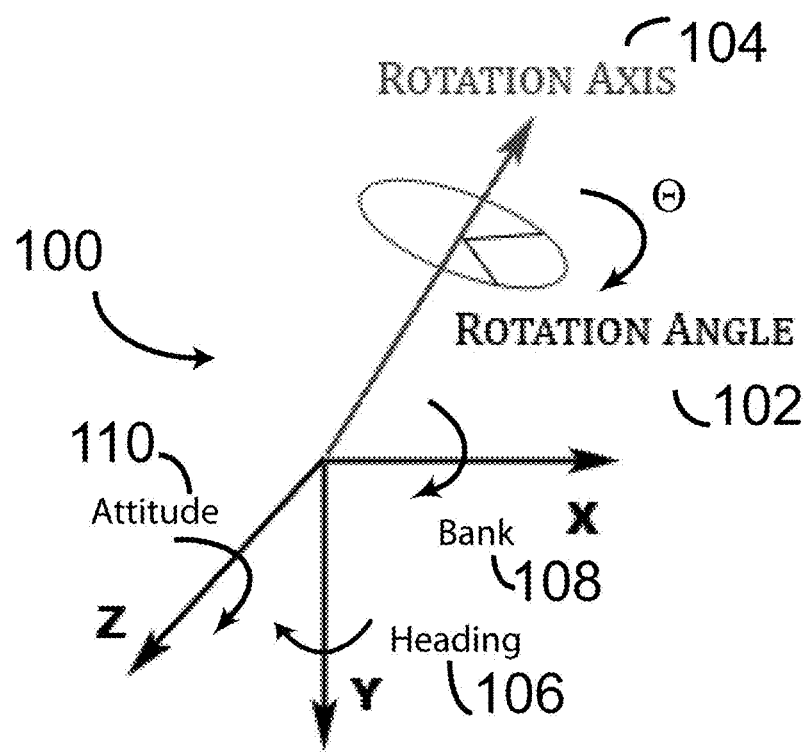
FIG. 1 is a diagram that illustrates the basic axes angles measured by the sensors according to one embodiment.

A sensor-based system and method for evaluating and enhancing postural control and balance in sports activities will now be described with reference to the drawings. Where possible, the same reference numbers are used throughout the drawings to refer to the same or like components. This description is intended to illustrate certain embodiments, but other embodiments that are apparent to those of ordinary skill in the art, including embodiments which do not provide all of the benefits and features set forth herein, are also within the scope of this invention. Thus, nothing in this detailed description is intended to suggest that any particular feature or component is essential. The invention is defined by the claims.

1. Overview

Embodiments of the present invention relate to sensor-based systems and methods for evaluating and enhancing postural control and balance in sports activities (e.g., golf, tennis, baseball, hockey, etc.). From the postural-control standpoint, with respect to golf for example, it has been suggested that the ground reaction force (GRF), the position of the center of mass (COM), and the fluctuation of foot pressure could be used to quantify postural control during the swing. Although measuring GRF has been cited in several publications, very few studies have explored the variation of the position of center of mass (COM) in a sport activity such as a golf swing. On the other hand, COM position is generally a key parameter in characterizing appropriate postural control. At this point, the state of the art does not provide a solution on how to:

1. Accurately measure the movement of a person's COM during a swing in real-life conditions and/or in real-time using a low-cost and easy-to-use system that minimally interferes with the sport activity itself. In-the-field measurements of COM are currently difficult to implement. Further, while some techniques can accurately measure the COM position during quiet standing, they have significant inaccuracies in measuring COM position during a sport motion (e.g., a swing motion).

2. Objectively and reliably separate a sport activity or motion into distinct temporal phases (e.g., for golf: the back swing, the down swing, the top of the back swing, the time of contact with the ball, the time of maximum speed of the COM, and the location at which the arm has its maximum speed in reference to COM).

3. Use the information gained from the above steps to help a person improve his or her postural control to have a better motion such as a better golf swing.

Until recently, measurement of body motion under real-life conditions has been difficult and impractical. Traditionally, balance has been assessed using laboratory-based systems such as optical motion measurement systems and force platform in a gait laboratory. While these systems are clinically accepted as "the gold standard," several drawbacks render them unsuitable for clinical and sports applications. Specifically, currently-available motion-analysis systems are time-consuming, expensive, and require an existing infrastructure and highly-trained personnel.

The recent emergence of body-worn sensor technology has provided new ways to measure and assess motor functions, including balance and physical activity. In particular, the combination of accelerometers with angular-rate sensors (gyroscopes) holds great promise for hybrid kinematic sensor modules that measure the three-dimensional kinematics of body segments. Three key advantages render body-worn sensors ideal tools for developing clinical and sports-training applications: (1) they are inexpensive; (2) they are lightweight and portable; and (3) they do not require a specific environment or installation of any particular infrastructure. Body-worn sensors consequently have tremendous potential for enabling physicians/trainers to evaluate postural control under real conditions by quantifying its subcomponents, such as body-segment kinematics data, kinetic data, and (feedforward) motor adaptation.

2. Posture Control and Balance Evaluation System Overview

Embodiments of the invention are directed to an innovative, portable, and cost-effective body-worn sensor-based system to evaluate the biomechanics and the motor adaptation characteristics of postural control during a sport activity such as a golf swing. Various embodiments use the above described recently available sensor technology such as accelerometers, gyroscopes, and magnetometers to measure the three-dimensional motion of ankle and hip joints. In one embodiment, the sensors may be embedded in a device such as a smartphone carried by the person or embedded into the clothing of the person. In several embodiments, additional sensors could be attached to other body segments to improve the accuracy or to measure particular instants during a golf swing, such as the top of back swing, the instant of the maximum speed of arm, and the instant of impacting the ball. In one embodiment applied to golf, the system combines the measured data in conjunction with a biomechanical model of the human body to:

1. Estimate the two-dimensional sway (i.e., movements back and forth, or sideways) of the golfer's COM. This is a by-product of finding the position of the COM over time using the n-link models (n=1, 2, 3, . . . etc.).

2. Quantify and evaluate the golfer's overall balance via his/her postural compensatory strategy (i.e., how the movement of the upper limbs compensates for the movement of lower limbs in an attempt to optimize postural control during the swing and to maximize the power of the swing).

3. Provide feedback to the golfer for improving his or her dynamic postural control, using an interface (e.g., a visual interface; see, e.g., FIG. 6). In one embodiment, the system uses the golfer's estimated COM position at specified time points during the swing phase. Examples of chosen time points are: the instant when the hand velocity during the downswing is at its maximum; the top of the down-swing; and the time of impact with the ball.

Figure 14:
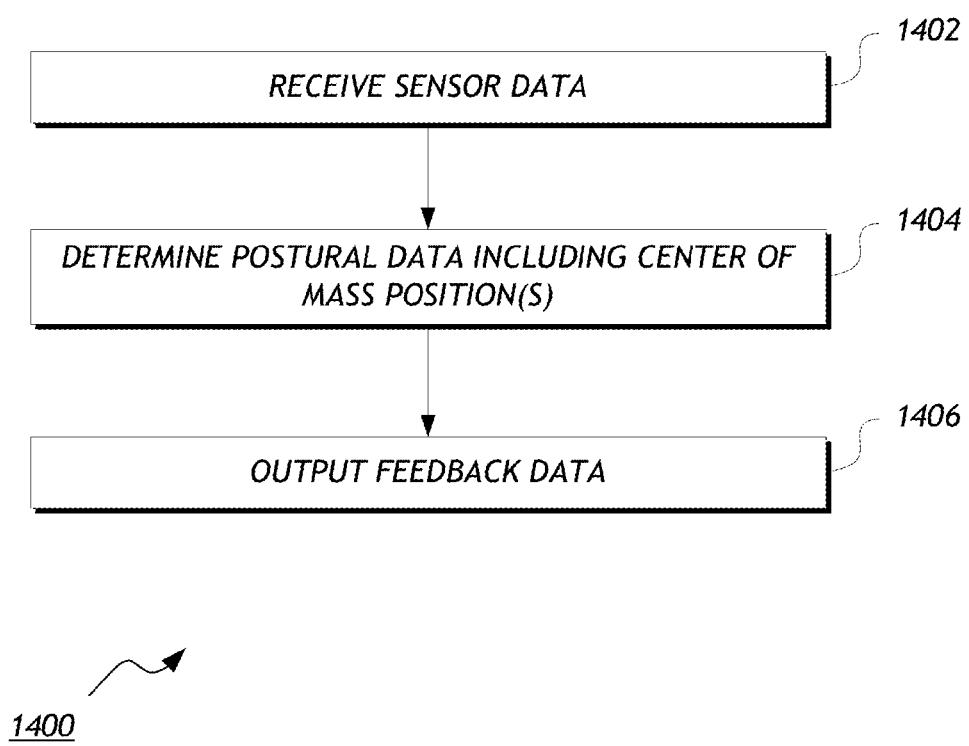
FIG. 14 is a flow diagram illustrating a postural and balance evaluation method in accordance with one embodiment.

FIG. 14 is a flow diagram illustrating a postural and balance evaluation method 1400 in accordance with one embodiment. At block 1402, sensor data is received. The sensor data may include data collected from sensor(s) worn by the person engaged in a sport activity. At block 1404, the system may determine postural data including COM position(s) of the person engaging in the sport activity. The term "determine" as used herein should be broadly interpreted to mean any method of determining the COM positions, including deriving the actual COM positions as well as estimating the COM positions. As will be further described, the COM positions may be determined based on a single-link model (treating the body as a single segment) or a multi-link model (separating the body into multiple segments with postural/movement/position data associated with each). In one embodiment, a multi-link model is used to account for movement around certain body joints such as hips, ankles, and knees. In one embodiment, the COM position(s) are determined at various temporal phases of a particular sport motion within the activity (e.g., swing of the golf club, swing of the baseball bat, swing of the tennis racket, etc.). The temporal phases may be pre-defined to capture certain portions of the motion that have been deemed critical to improved performance or user-defined (e.g., to allow a user to focus on his or her areas of weaknesses). For example, in baseball and tennis, one COM position that is particularly relevant to improved performance is the COM position when the arm speed is at a maximum. At 1406, in one embodiment, feedback data is outputted by the system. The feedback data may be provided in one embodiment via a user interface display. The feedback data in one embodiment includes a comparison of a determined COM position with an ideal COM position. The ideal COM position may be determined based on sensor data collected when the user is in a standing position (e.g., standing upright for a few seconds and not engaged in the sport activity/motion). In one embodiment, the postural data and/or feedback data may be stored in a mass storage within the system or remotely on a server. The stored postural and/or feedback data may be combined with data related to a future performance of the sport activity to support data tracking and analysis for improved performance of the sport activity.

Figure 2:
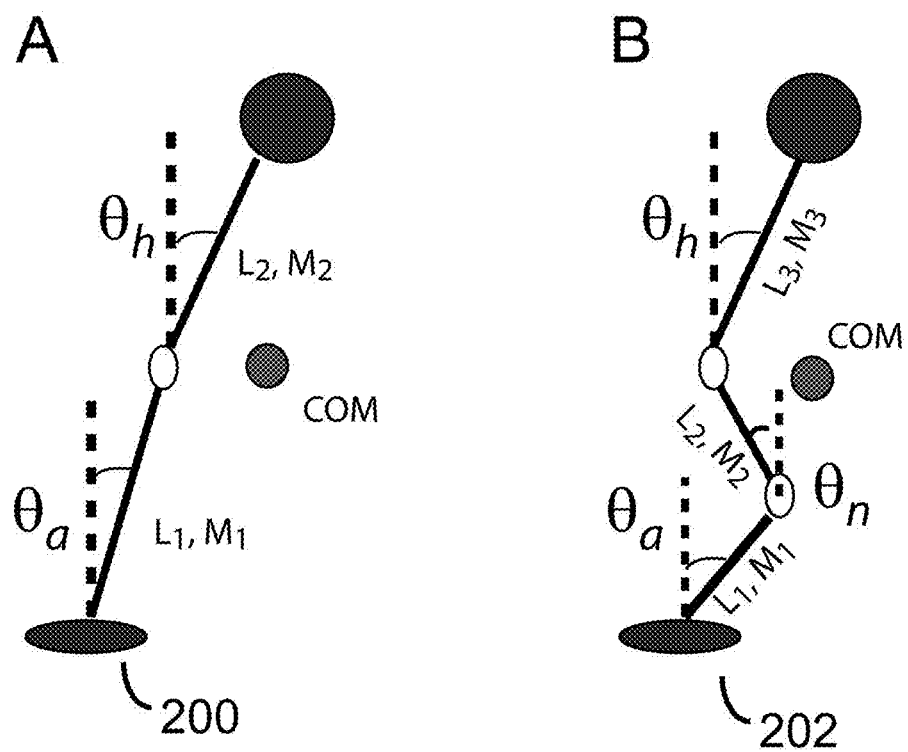
FIG. 2 is a diagram that depicts an example two-link and three-link model for estimating COM trajectory according to one embodiment.

FIG. 2 depicts two biomechanical models of the human body that could be used for any or all of the above listed operations. Depicted in the figure are a two-link model 200 and a three-link model 202. For example, during a golf swing, the motion of hip joint cannot be neglected compared to the ankle motion. To overcome this shortcoming, a two- or three-segment model of the body is used in some embodiments to calculate the anterior-posterior (A-P) and medial-lateral (M-L) angles during the movement. The use of these models in various embodiments will be further described below. In addition, any or all of the above operations may be done in either real-time or offline.

Embodiments of the invention allow physicians and/or trainers to carry out several tasks under real-life and/or real-time conditions which have not been possible before. First, they can obtain accurate and objective assessments of postural control by the user in real-life conditions. Second, they can use the various embodiments of the present invention to analyze feedforward processes that shape motor action on the basis of previously executed actions. In addition to golf, various embodiments of this invention are useful for assessing the balance of patients suffering from a variety of balance control disorders. For example, an embodiment of this invention may be a useful tool in studying learning and memory disorders and the design of optimally-efficient training paradigms.

As another example, various embodiments of this invention can implement motor-adaptation paradigms that will be designed and used to analyze specific feedforward processes. For example, an important obstacle in exploring the motor learning process in golfers is the unavailability of a low-cost and easy-to-use technology allowing the analysis of motor response to sensory feedback cues. Various embodiments of this invention employ MEMS technology (e.g., the sensors can be MEMS-based) combined with a novel biomechanical model of the human body to quantify and improve the postural control during golf swing. One embodiment of the invention 1) estimates the user's COM position at particular moments during the down-swing phase; 2) characterizes COM trajectory to assess the quality of the swing; and 3) provides visual feedback, for the user, on the position of the COM at particular moments during the swing (e.g., the position of COM at maximum arm speed during down-swing phase) with respect to predefined positions. In one embodiment, the positions can include positions such as (1) the position of COM during upright position, (2) at the "address" position (i.e., when the player is standing ready at the ball and about to begin the swing), (3) at the top of the backswing, and (4) at the time of impact. In one embodiment, the position can be user-defined.

3. Mechanics of the Model(s)

3.1. Estimation of the Angles

With reference to FIG. 1, in one embodiment, each sensor is configured to provide quaternions (qw, qx, qy, qz) that are subsequently converted to Euler angles ($\theta$, $\phi$, $\psi$). The resulting three-dimensional angles are used to estimate the trajectory of the user's hand, ankle, hip, and COM during the swing. The Euler angles, used to describe a sequence of three rotations determining the orientation of a rigid body in three dimensions, are (in their order of application): i) Heading 106 ($\theta$); ii) Attitude 110 ($\phi$); and iii) Bank 108 ($\psi$). It should be noted that the choice of the X-Y-Z coordinate system about which the heading, attitude, and bank angles are defined is arbitrary, and FIG. 1 illustrates one such choice.

In one embodiment, the quaternion output of the calibrated sensor during the swing, $q_{FINAL}$, is converted to the Euler angles as follows:

$$q_{FINAL} = q_w + q_x i + q_y j + q_z k$$

$$\theta = a\tan\left[\frac{2 \cdot q_y \cdot q_w - 2 \cdot q_x \cdot q_z}{1 - 2 \cdot q_y^2 - 2 \cdot q_z^2}\right]$$

$$\varphi = a\sin(2 \cdot q_x \cdot q_y - 2 \cdot q_z \cdot q_w)$$

$$\Psi = a\tan\left(\frac{2 \cdot q_x \cdot q_w - 2 \cdot q_y \cdot q_z}{1 - 2 \cdot q_x^2 - 2 \cdot q_z^2}\right)$$

In the above equations, $q_x$, $q_y$, $q_w$, and $q_z$ represent the components of the quaternion output $q_{FINAL}$.

3.2. Estimation of the Displacement from the Angles

Several ways exist for estimating the COM of the user during the swing. For example, in a well-known method in gait analysis, one can use the acceleration signal obtained from a sensor placed on the sacrum of the user, often the best position to monitor the COM. Although this approach may produce accurate results during quiet standing or walking on a straight line, it may be inappropriate for assessing the COM during a swing. This approach assumes a single invert pendulum model in which body mass rotates around the ankle joint (assuming a negligible motion of a hip joint.)

During a golf swing, however, the motion of hip joint cannot be neglected compared to the ankle motion. To overcome this shortcoming, in one embodiment, a two- or three-segment model of the body is used to calculate the anterior-posterior (A-P) and medial-lateral (M-L) angles during the movement.

3.2.1. The Single-Link Model for Estimating the Position of the COM

Figure 3:
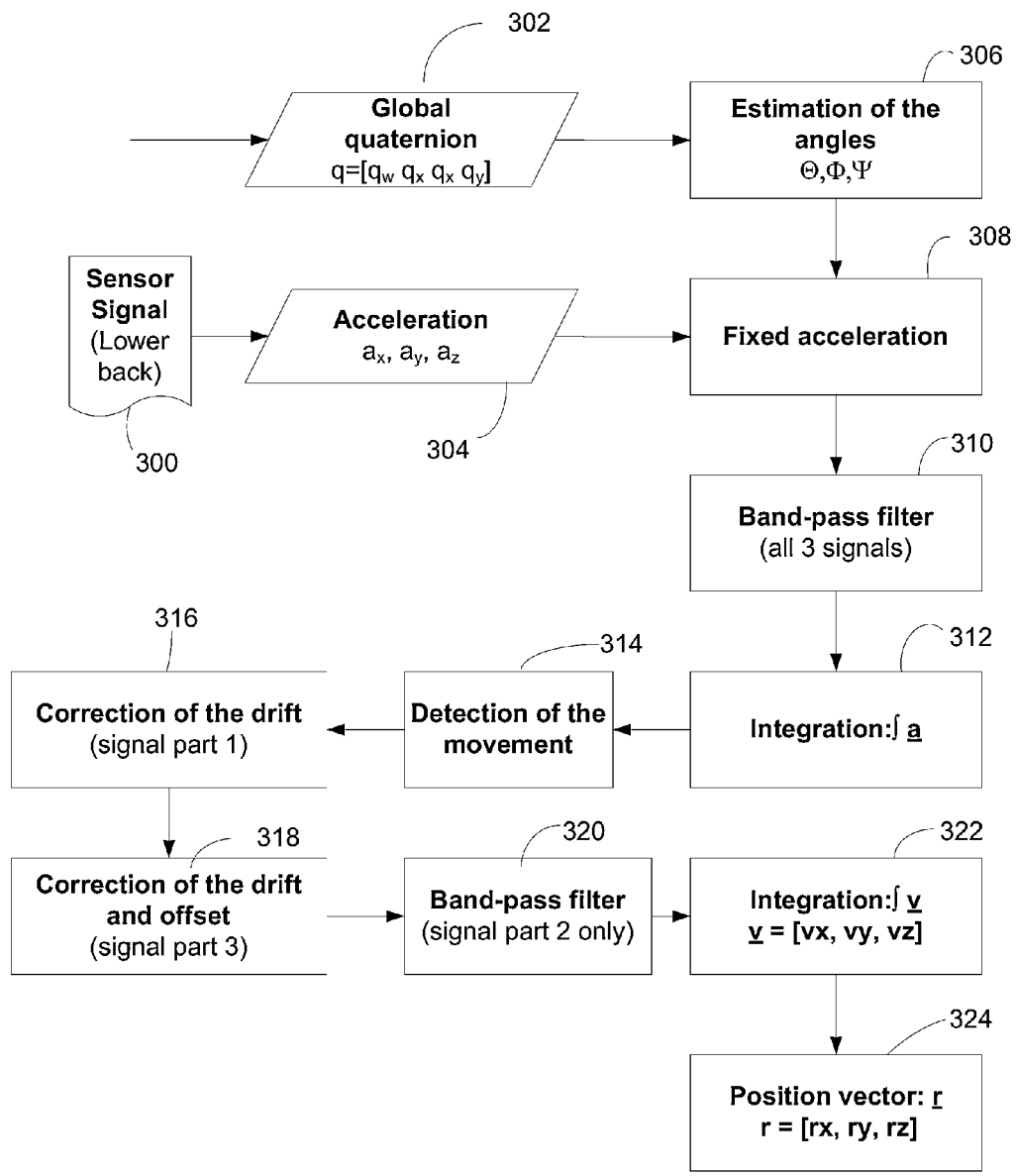
FIG. 3 is a flow diagram depicting a process for estimating the position of COM based on a single-link model in accordance with one embodiment.

FIG. 3 depicts an example method for estimating the position of the COM based on a single-link model. Although the depicted example method is based on a single-link model, portions of the method are applicable to multi-link models such as the two-link and three-link models, as further described below. Block 300 shows the receipt of a sensor signal (e.g., from a sensor affixed to the lower back region of the user). The sensor signal is fed to processes 302 and 304 to extract the global quaternions and accelerations. Angles are estimated in block 306 based on the global quaternions. The calculations result in fixed acceleration in block 308, since the acceleration in each axis needs to be expressed in a fixed frame. To accomplish this, in one embodiment, the quaternion output of each sensor is transformed via a rotation matrix $M_{ROTATION}$. For a local calibration of the sensor placed at the sacrum of the user (Y-axis oriented downwards—see FIG. 1), the acceleration vector can be expressed as:

$$\begin{pmatrix} a_{x-fixed} \\ a_{y-fixed} \\ a_{z-fixed} \end{pmatrix} = M_{ROTATION} \cdot \begin{pmatrix} a_x \\ a_y \\ a_z \end{pmatrix} + \begin{pmatrix} 1 \\ 0 \\ 0 \end{pmatrix}, \text{ where}$$

$$M_{ROTATION} = \begin{bmatrix} 1 - 2q_y^2 - 2q_z^2 & 2q_xq_y - 2q_zq_w & 2q_xq_y + 2q_yq_w \\ 2q_xq_y + 2q_zq_w & 1 - 2q_x^2 - 2q_z^2 & 2q_yq_z - 2q_xq_w \\ 2q_xq_z - 2q_yq_w & 2q_yq_z + 2q_xq_w & 1 - 2q_x^2 - 2q_y^2 \end{bmatrix}$$

The acceleration values are normalized by the value of the gravitational constant g, and thus are unitless.

In one embodiment, next, in block 310, the fixed accelerations (three signals in the x, y, and z directions, respectively) are filtered with a band-pass filter (e.g., a wavelet) to remove the DC component. After filtering, in block 312, a trapezoidal integration routine is used to compute the velocity of the movement. Even for this relatively fast motion, the resulting integration can exhibit some drift. The drift can be represented as an offset $E$ added to the value of the acceleration:

$$v(t) = \int_{t_0}^{t} (a(u) + \epsilon) \cdot du$$

Figure 5:
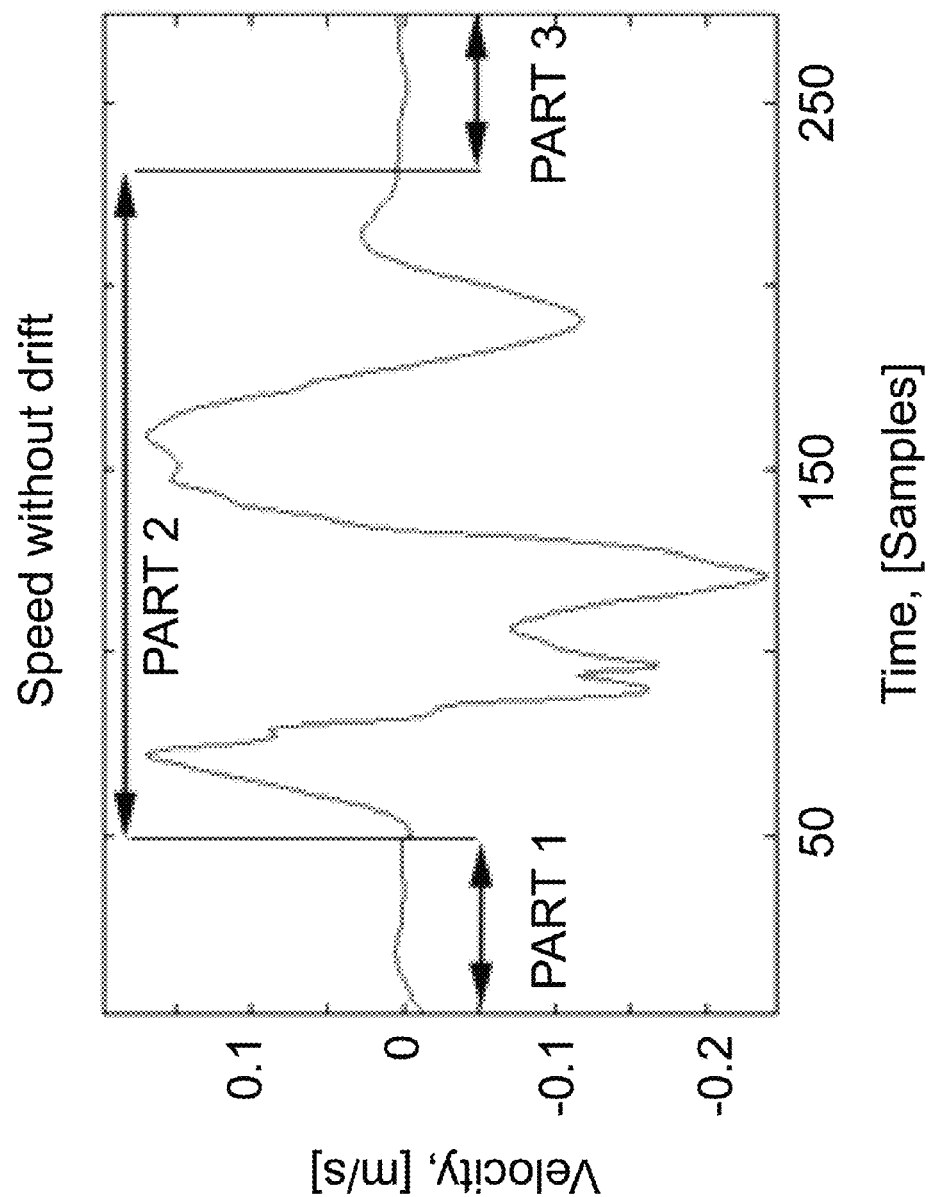
FIG. 5 shows a graph that depicts the pattern of speed estimated from integration of acceleration in a fixed frame in accordance with one embodiment.

Drift can be removed in several ways. In one embodiment, it can be assumed that velocity is nearly zero at the beginning and the end of the swing motion. To identify the zero velocity segments at the beginning and the end of the swing, one embodiment searches those periods in the beginning (i.e., the "address position," which is conventionally defined as the position a golfer takes as he or she stands over the ball, ready to swing) and the end of the swing (i.e., impact) in which a segment of velocity data composed of at least 10 consecutive samples that produces a standard deviation of less than a fixed threshold value (less than 0.001 m/s.) In one embodiment, the beginning and the end of swing are automatically identified using the signals extracted from the sensor attached to the arm. In one embodiment, this is based on the arm position at address. The beginning of the swing is defined as the first movement of the arm in one embodiment. In one embodiment, impact determines the end of the swing. The top of the backswing is defined as the point where the COM changes directions in the side-to-side motion. These assumptions and definitions enable the definition of three segments during the swing: 1) the beginning of the swing; 2) the swing itself; 3) and impact, as depicted by the three parts in the graph shown in FIG. 5. The graph in FIG. 5 shows the pattern of speed estimated from integration of acceleration in a fixed frame.

Thus one embodiment includes an algorithm designed to identify those parts by assessing the standard deviation of the velocity at the beginning and the end of swing. These parts of the signal are used to estimate the drift of integration.

The detection of the movement at block 314 helps identify the three parts as discussed above. The detection of the movement assumes that before starting the swing, the user is at the rest position (no movement). In one embodiment, identifying this period is critical for removing the drift that gets added during the integration step. To identify the rest period, the system in one embodiment detects the initiation of movement via the estimated velocity and then assumes that, during the few points prior to that instant, the user was at rest (velocity=0). With the three parts identified, returning to FIG. 3, in block 316, the drift of the first part of the speed (beginning of the swing) is calculated and removed from the whole signal. Then, in block 318, the drift of the third part (at impact) is estimated and removed. In block 320, a band-pass filter is used for the second and last remaining part of the speed (the part that covers the swing itself).

Finally, once drift has been removed from the velocity, the position of the COM (324) is found by integrating the velocity vector (block 322).

3.2.2. The Multi-Link Models for Estimating the Position of the COM

Figure 4:
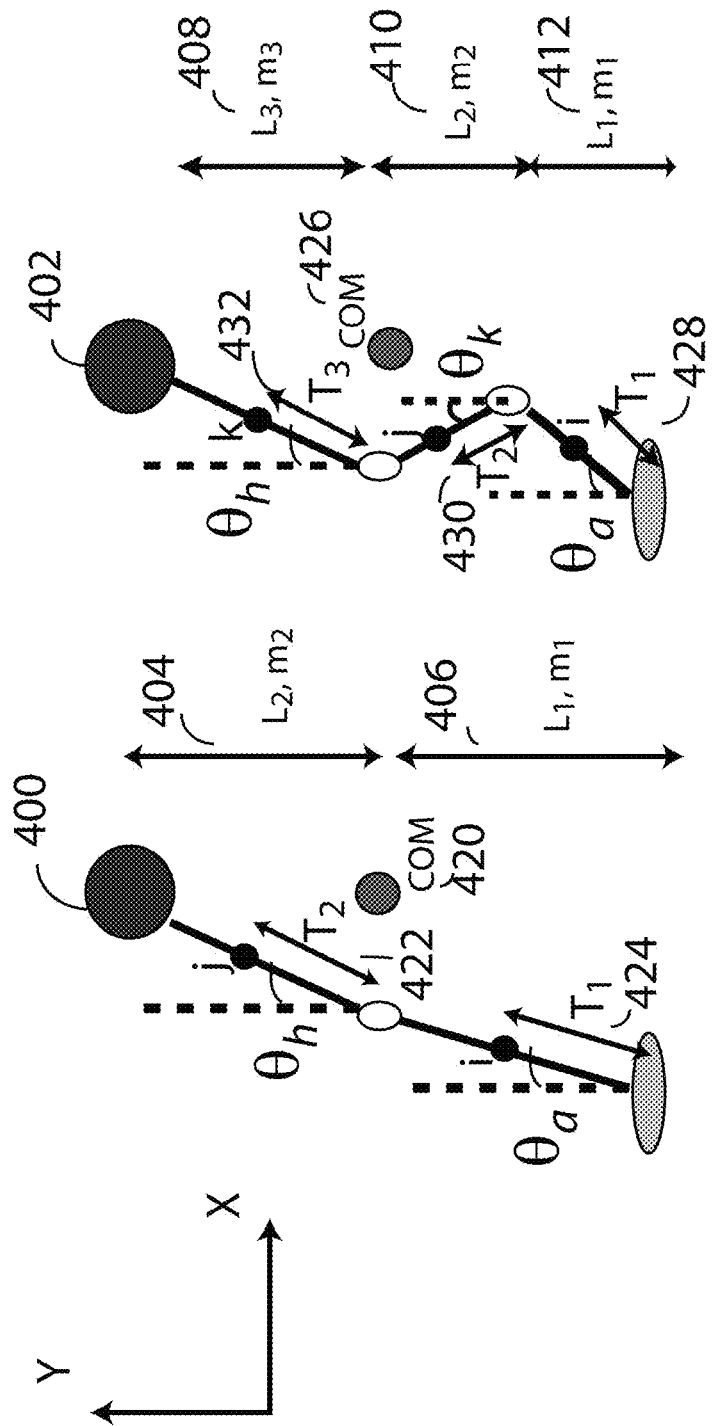
FIG. 4 illustrates an example estimation of COM based on a two-link model and a three-link model in accordance with one embodiment.
Figure 9:
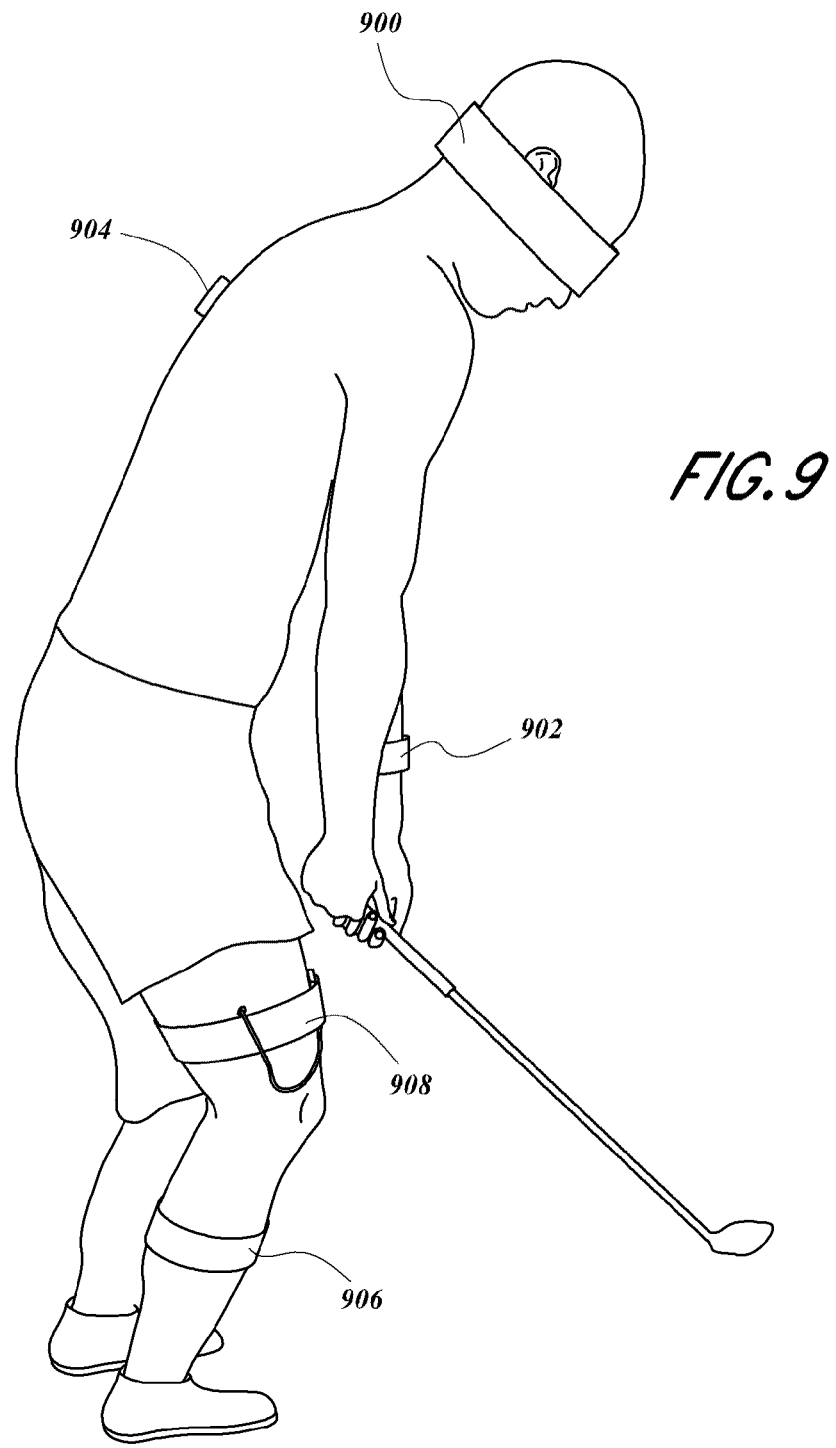
FIG. 9 illustrates a physical setup of the sensors in accordance with one embodiment.

FIG. 4 illustrates a two-link and a three-link model of the human body that can be used to estimate a person's COM once the joint angles are estimated, as described, for example, in Section 3.2 above. Anthropometric data provides the values for the parameters used for each segment. FIG. 9 illustrates an example of sensor attachment 900 for a three-link model. The sensors attached to the user's shin (906), thigh (908), and back (904) provide, respectively, the angle of ankle ($\theta a$), knee ($\theta k$) and hip ($\theta h$) joints in the anterior-posterior (A-P) plane, as illustrated in the representative human body FIG. 402 within FIG. 4. Note that in other embodiments, the positions of the sensors may be different, or the sensors may be embedded into clothing worn by the person at those specific positions. Having the anthropometric data of each user (e.g., body mass m and height H), the position of each link's COM in the sagittal plane can be described as:

$$\vec{i} = (T_1 \cdot \sin\theta_a, T_1 \cdot \cos\theta_a) \vec{j} = (L_1 \cdot \sin\theta_a + T_2 \cdot \sin\theta_k, L_1 \cdot \cos\theta_a + T_2 \cdot \cos\theta_k)$$

$$\vec{k} = (L_1 \cdot \sin\theta_a + L_2 \cdot \sin\theta_k + T_3 \cdot \sin\theta_t, L_1 \cdot \cos\theta_a + L_2 \cdot \cos\theta_k + T_3 \cdot \cos\theta_t)$$

$$\vec{COM} = \left( \frac{m_1 \cdot \vec{i}_x + m_2 \cdot \vec{j}_x + m_3 \cdot \vec{k}_x}{m_1 + m_2 + m_3}, \frac{m_1 \cdot \vec{i}_y + m_2 \cdot \vec{j}_y + m_3 \cdot \vec{k}_y}{m_1 + m_2 + m_3} \right)$$

Here, $\theta_a$, $\theta_k$, and $\theta_t$ represent, respectively, the angular displacement of the ankle, knee, and trunk (as shown in the human body FIG. 402 in FIG. 4). The first component of the COM corresponds to the frontal direction or movement in anetior-posterior (A-P direction), which can be expressed as:

$$\vec{COM} = \frac{1}{m_1 + m_2 + m_3} \cdot (m_1 \cdot T_1 \cdot \sin\theta_a + m_2 \cdot (L_1 \cdot \sin\theta_a + T_2 \cdot \sin\theta_k) +$$

$$m_3 \cdot (L_1 \cdot \sin\theta_a + L_2 \cdot \sin\theta_k + T_3 \cdot \sin\theta_t) =$$

$$\frac{1}{m_1 + m_2 + m_3} \cdot ((m_1 + T_1 + m_2 \cdot L_1 + m_3 \cdot L_1) \cdot \sin\theta_a +$$

$$(m_2 \cdot T_2 + m_3 \cdot L_2) \cdot \sin\theta_k + m_3 \cdot T_3 \cdot \sin\theta_t)$$

The equations can be rewritten with three constants, as follows:

$$\vec{COM} = K_1 \cdot \sin\theta_a \alpha K_2 \cdot \sin\theta_t$$

where $$K_1 = \frac{m_1 \cdot T_1 + m_2 \cdot L_1 + M_3 \cdot L_1}{m_1 + m_2 + m_3},$$

$$K_2 = \frac{m_2 \cdot T_2 + m_3 \cdot L_2}{m_1 + m_2 + m_3}, \text{ and } K_3 = \frac{m_3 \cdot T_3}{m_1 + m_2 + m_3}$$

The equation of the COM in the medial-lateral direction (M-L) direction can be derived in an analogous fashion, with the angles expressed in the M-L direction.

A similar analysis for the two-link model provides the following relationships:

$$\vec{COM} = K_1 \cdot \sin\theta_a \alpha K_2 \cdot \sin\theta_t$$

where $$K_1 = \frac{m_1 \cdot T_1 + m_2 \cdot L_1}{m_1 + m_2}, \text{ and } K_2 = \frac{m_2 \cdot T_2}{m_1 + m_2}$$

The values of $m_i$ and $T_i$ (i=1-3), and $L_j$ (j=1, 2), can be estimated from user's body mass and height as explained by D. Winter et al., Biomechanics and motor control of human movement. New York: Wiley, 1990, the disclosure of which is hereby incorporated by reference. In one embodiment, the system described herein obtains the user body mass and height as part of an initial set up process (e.g., via an input in a displayed user interface). Those skilled in the art will appreciate that aspects of the sample single-link based COM determination method shown in FIG. 3 such as drift correction are applicable to the two- or three-link model based COM calculations as well.

4. Providing a Visual Feedback of the Swing to the User

An embodiment of the present invention provides the user with visual feedback about his or her postural control during the golf swing. Embodiments of the invention take advantage of the observation that the position of the COM at certain time points can be used to describe an ideal swing, and provide those positions of the COM to the user to help improve the swing. These time points include, but are not limited to: (1) the instant of maximum arm speed; (2) the instant at which the golfer assumes the address position; and (3) the instant of starting the down-swing phase.

In one embodiment, these time points can be identified using a sensor attached to the user's arm (e.g., sensor 902 as shown in FIG. 9). In one embodiment, the system computes the position of the user's COM at such specified time points, using data measured by the sensors during the swing. Next, the system compares the position of the COM at the specified times with the "reference"/"target" positions of the COM. In one embodiment, the reference position is defined as the COM position when the user is in the neutral standing position. This position can be estimated, for example, during an initial calibration in which the user is requested to be at upright position without any motion for a period of approximately 5 seconds. The user is then provided with feedback through an interface (e.g., visual and/or audio) about the estimated actual position of his or her COM relative to the reference COM positions. The system may then instruct the user on how to reduce the difference between the estimated actual position and the reference/target COM position.

Figure 6:
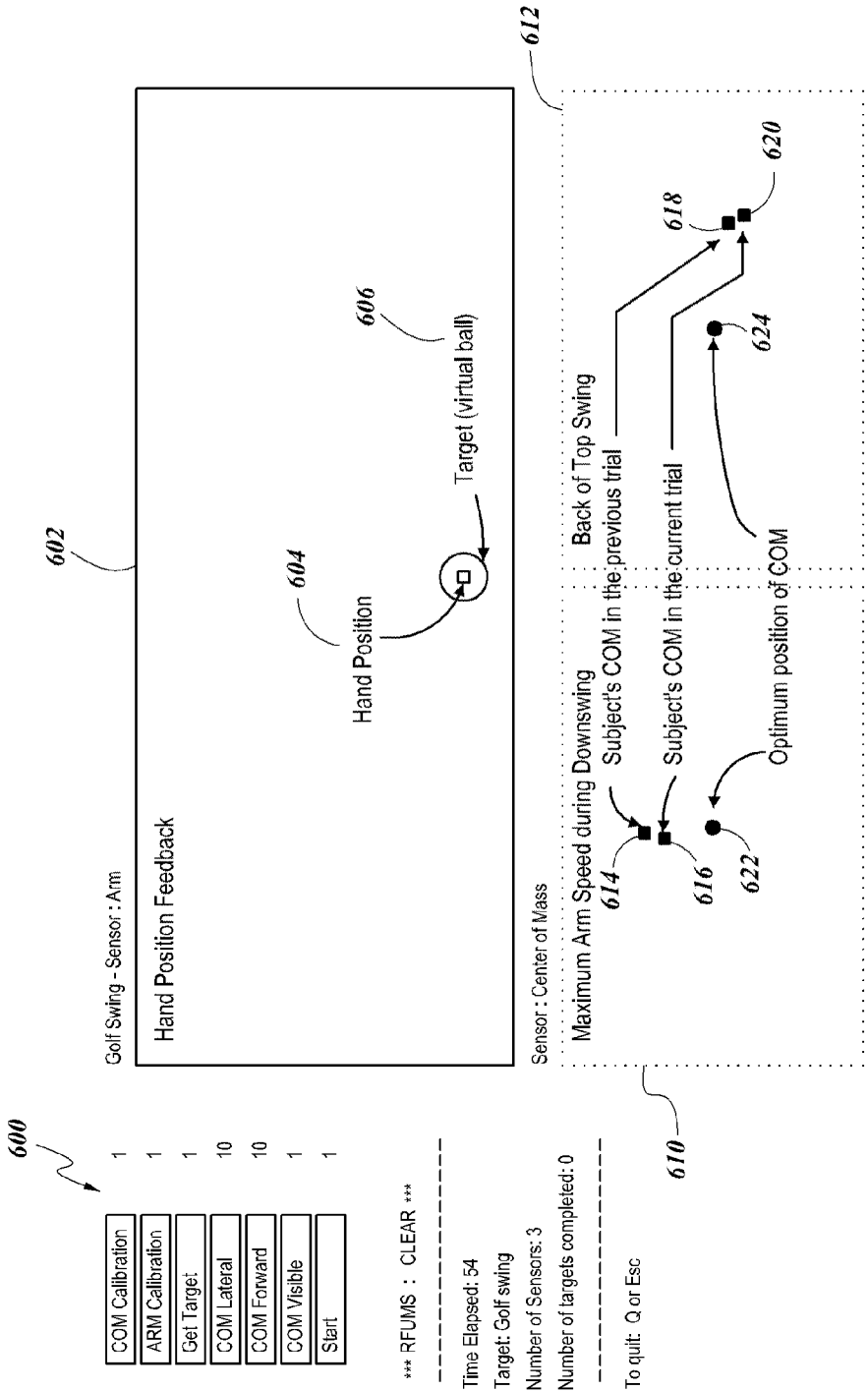
FIG. 6 shows an example user interface of a program that provides visual feedback on a golf swing in accordance with one embodiment.

FIG. 6 illustrates an exemplary interface 600 used to provide visual feedback to the user including the above information. In one embodiment, the interface 600 includes one or more of: an interface 602 based on data from a sensor worn on the person's arm, and interfaces 610 and 612 reflecting the COM of the person during various parts of the swing. In the example depicted, the interface 602 shows the position of the player's hand (604), which is used to assist him/her to hit a virtual ball (target) 606 displayed on the same screen. While a virtual ball is used here in this example, in other embodiments, a sensor may be attached to an actual golf ball or some other object such as the golf club and the interface 602 may be adapted to display the position of the sensor attached to the ball or some other object that stands in place of the ball.

In one embodiment, at the end of each trial, the position of the COM at specified instants of the backswing phase (612) and the downswing phase (610) are displayed to assist the player improve his or her postural control in subsequent trials. Note for example, the downswing phase interface 610 displays the positions of the COM from two trials 614 (previous) and 616 (current), along with the optimum position of the COM 622. A similar display in the backswing phase interface 612 shows the trial positions 618 (previous) and 620 (current) with the optimum position 624.

Figure 7:
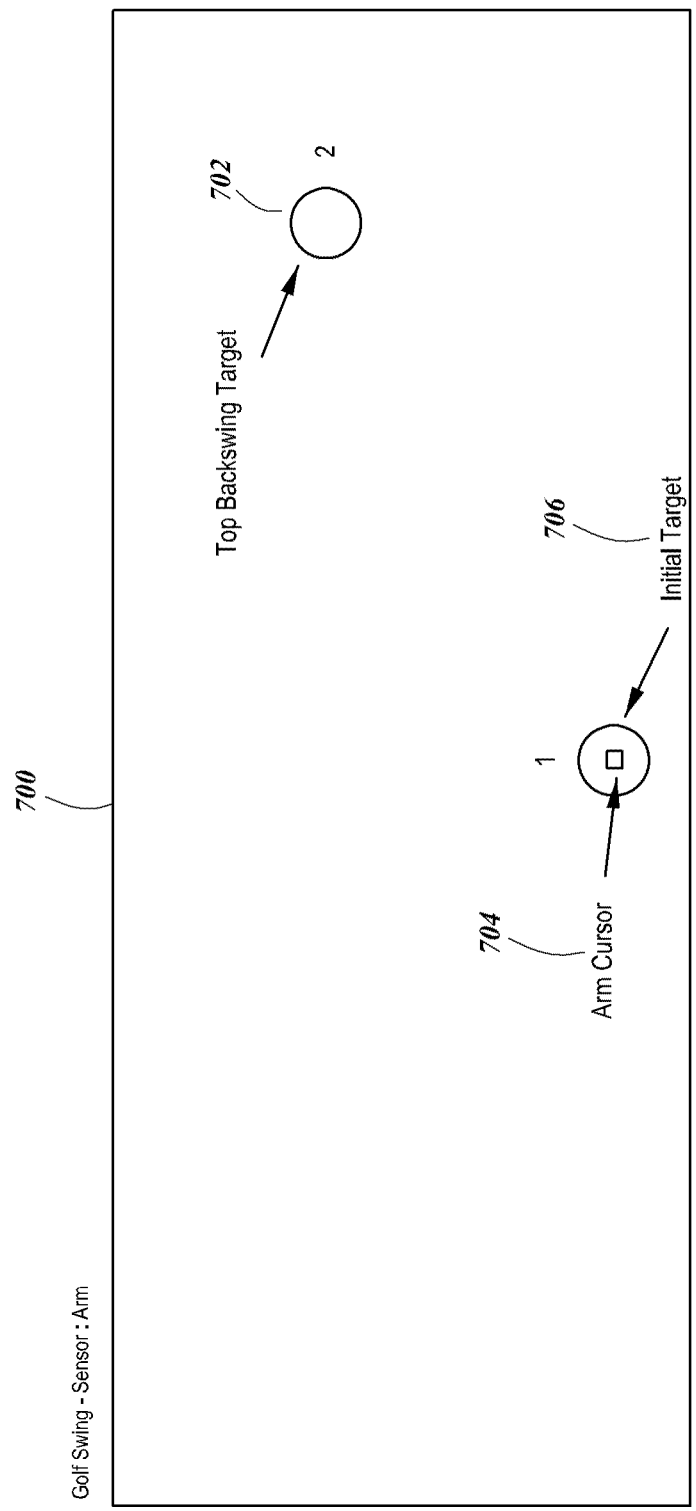
FIG. 7 shows an example user interface of a program that helps users identify a proper swing motion in accordance with one embodiment.

FIG. 7 illustrates an example user interface 700 showing an example arm trajectory during the swing. The interface identifies the initiation of the swing, the estimate of the top of the backswing, and the termination of the backswing (reaching back to the initial target). Based on the initial calibration of the sensor on the user's arm, the position of the arm is set inside of the initial target circle. This may be done by asking the user to bring the club at address and then have the system automatically set this position as initiation of the swing. The same process is done (optionally) for the backswing. In one embodiment, this calibration process needs to be performed only for the first trial and does not need to be re-performed for subsequent trials (except when the arm sensor has been moved).

As shown in FIG. 7, the "INITIAL TARGET" 706 represents a virtual golf ball, while the "ARM CURSOR" 704 (square cursor) reflects the position of the arm. At the beginning of the swing (i.e., Position "1"), the arm cursor rests in the middle of the INITIAL TARGET (which represents the approximate position of the ball). Once the arm cursor is in this position, the "TOP BACKSWING TARGET" 702 appears (Position "2"). With this visual indicator 702 now on display within the user interface 700, the user can then initiate his swing by moving his arm back and strive to reach the second target (i.e., "TOP BACKSWING TARGET"). Once the user reaches the second target with his motion, he can then initiate the second portion of the swing (the "downswing") and will move his arm forward and try to reach Position "1" (i.e., ball position).

Figure 8:
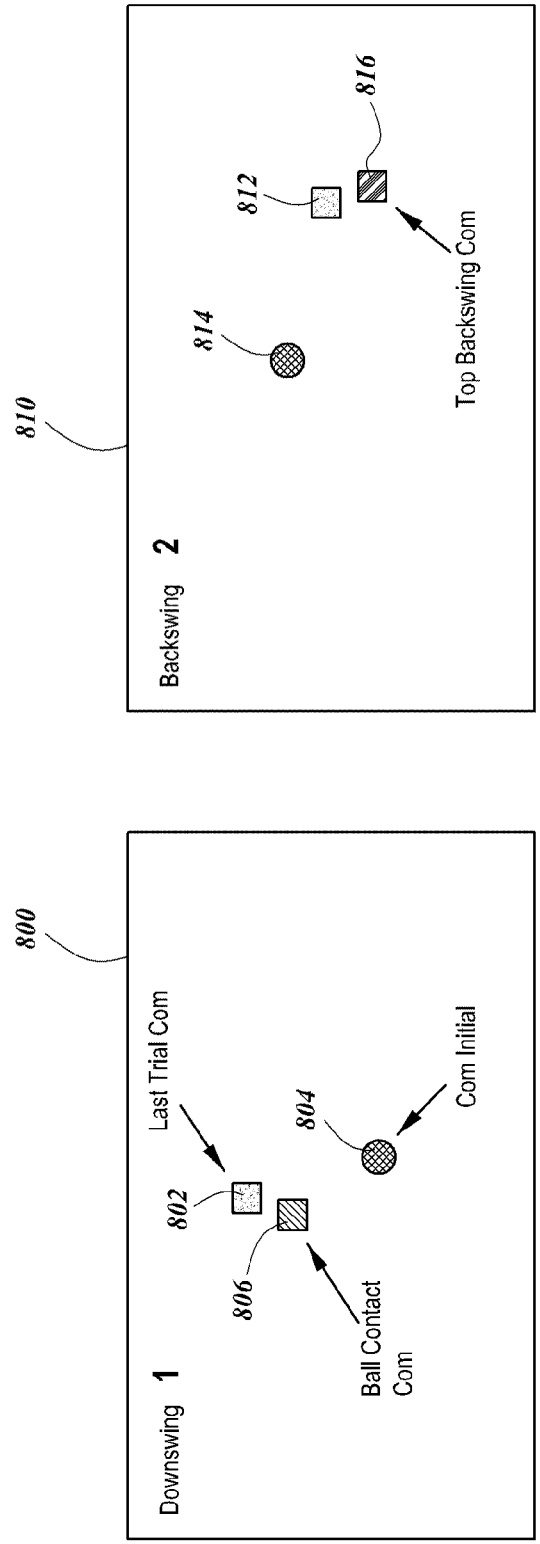
FIG. 8 illustrates an example COM-based feedback provided to a user to help improve the user's swing motion in accordance with one embodiment.

FIG. 8 shows an example user interfaces 800 and 810 that display visual feedback to the user at the end of the user's swing. In one embodiment, the combined user interfaces show the position of the user's COM at two times during the swing are displayed on the computer screen. As shown, in the user interface 810, the COM position at the top of the backswing 814 (t1) is shown to the user. In the user interface 800, the COM position at the moment when the arm has its maximum speed 806 (t2) is shown to the user.

In one embodiment, a target is displayed to show the user the ideal COM position (804 and 814). The display may also show the position of the COM during the last trial (802 and 812). At the end of each try, if the user has reduced the distance between his COM at times t1 and t2 and the ideal positions at those times, the user is notified via one or more visual and/or audio cues. For example, the COM target may change color, the COM target may "explode," and/or a sound may be played. By contrast, if the relevant distance at times t1 and t2 in the last try increases as compared with the second-to-last try, the user is notified in another manner (e.g., the COM target changes into another color).

5. Performance Metrics 5.1. COM Area and Norm of COM

Figure 10:
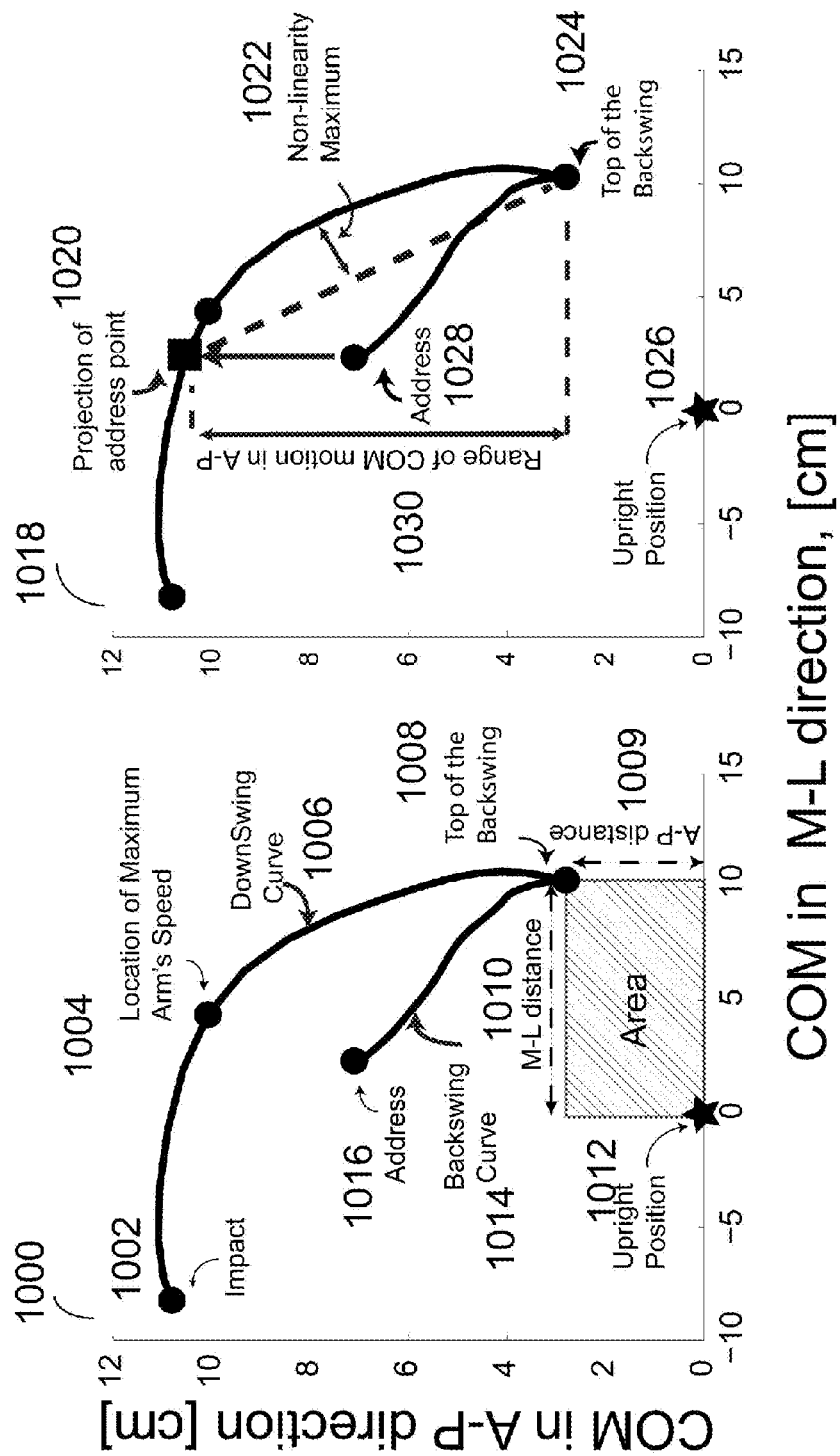
FIG. 10 shows two graphs depicting how a COM area is determined and how a non-linearity metric is determined according to one embodiment.

FIG. 10 shows a graph 1000 depicting how a COM area is determined according to one embodiment. Both graphs 1000 and 1018 are plotted with COM in the A-P direction in the Y-axis and COM in the M-L direction in the X-axis. Both illustrate the COM trajectory of a user from the beginning to the end of the golf swing. As depicted, the swing starts at the address position 1016, then the backswing curve 1014 shows the trajectory of the backswing going to the top of the backswing at 1008. Then the downswing curve 1006 shows the trajectory of the COM during the downswing from 1008 through the location at which the arm speed reaches a maximum (1004) all the way to impact with the golf ball at 1002. The ideal COM position 1012 is indicated by the star. One measurement of whether the swing is optimal is the COM area as shown. The COM area is obtained in one embodiment by multiply the A-P distance 1009 between the ideal COM and a particular COM during the swing and the M-L distance 1010 between the ideal COM and the particular COM during the swing (note than 1008 is chosen here as an example only).

Figure 11A:
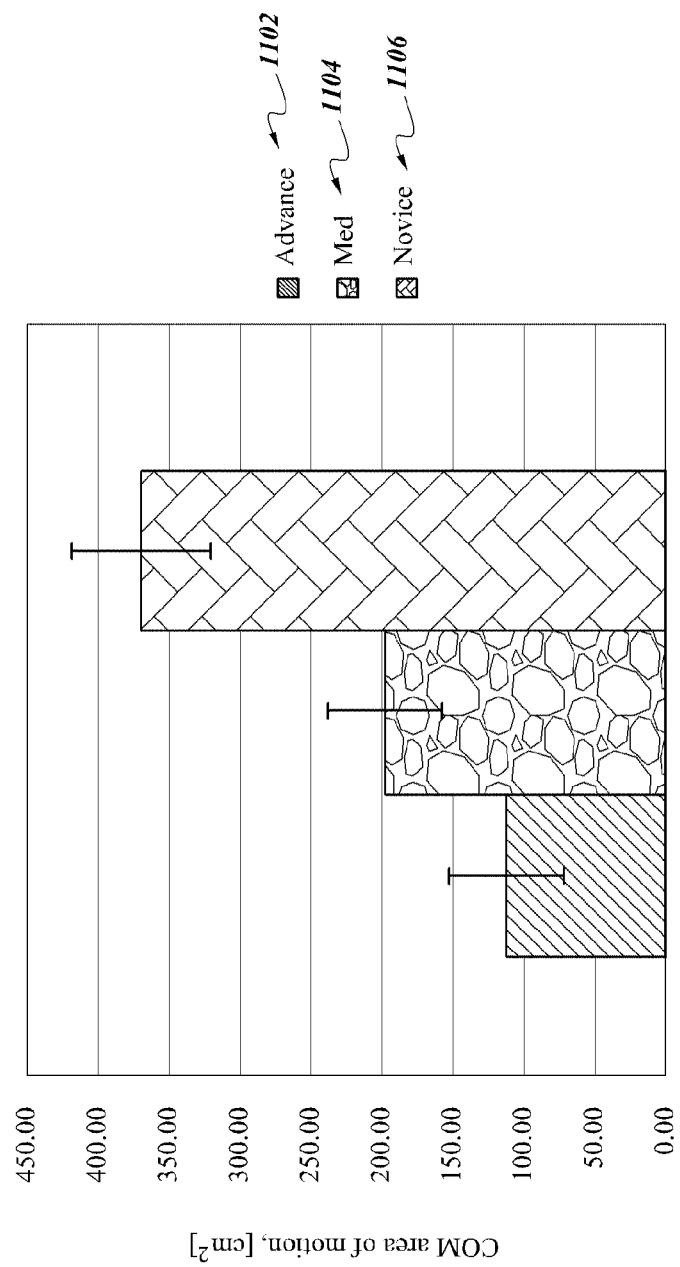
FIGS. 11A and 11B are graphs depicting the COM area of motion for various example swing motions.
Figure 11B:
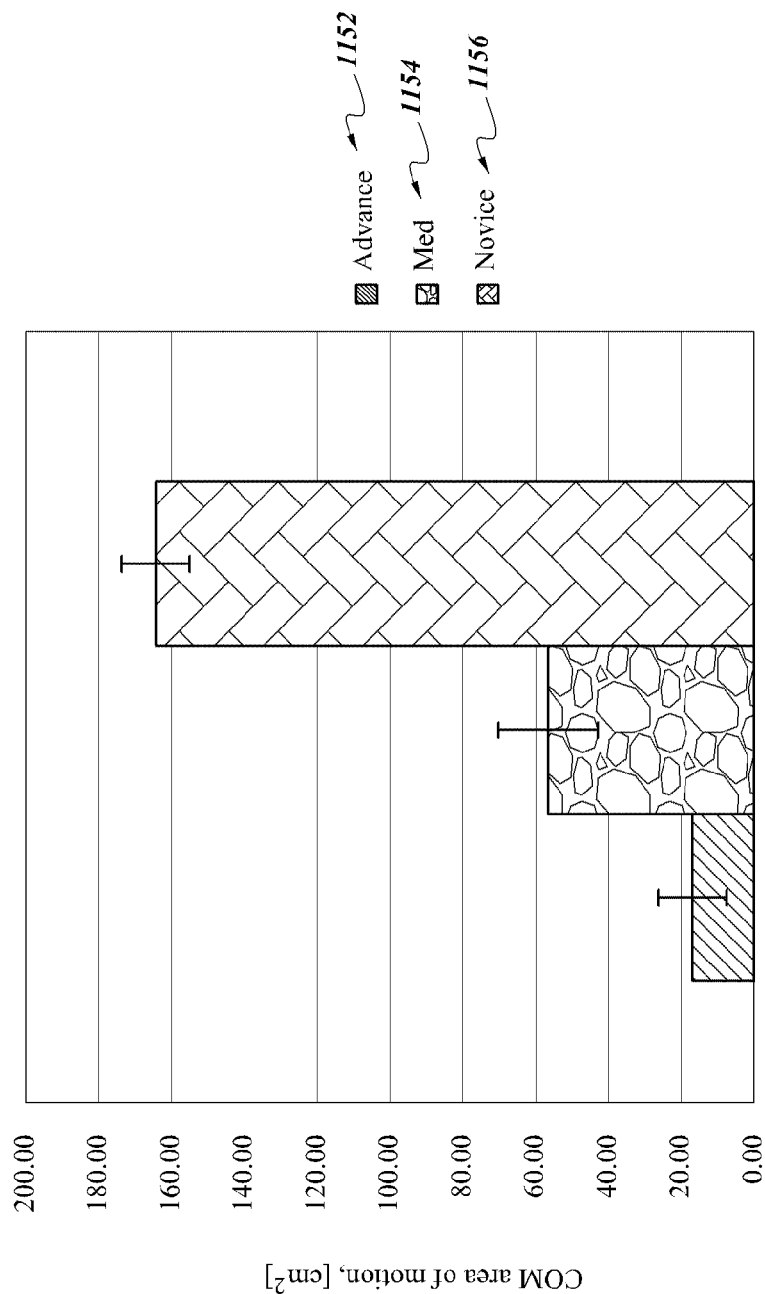
Figure 12:
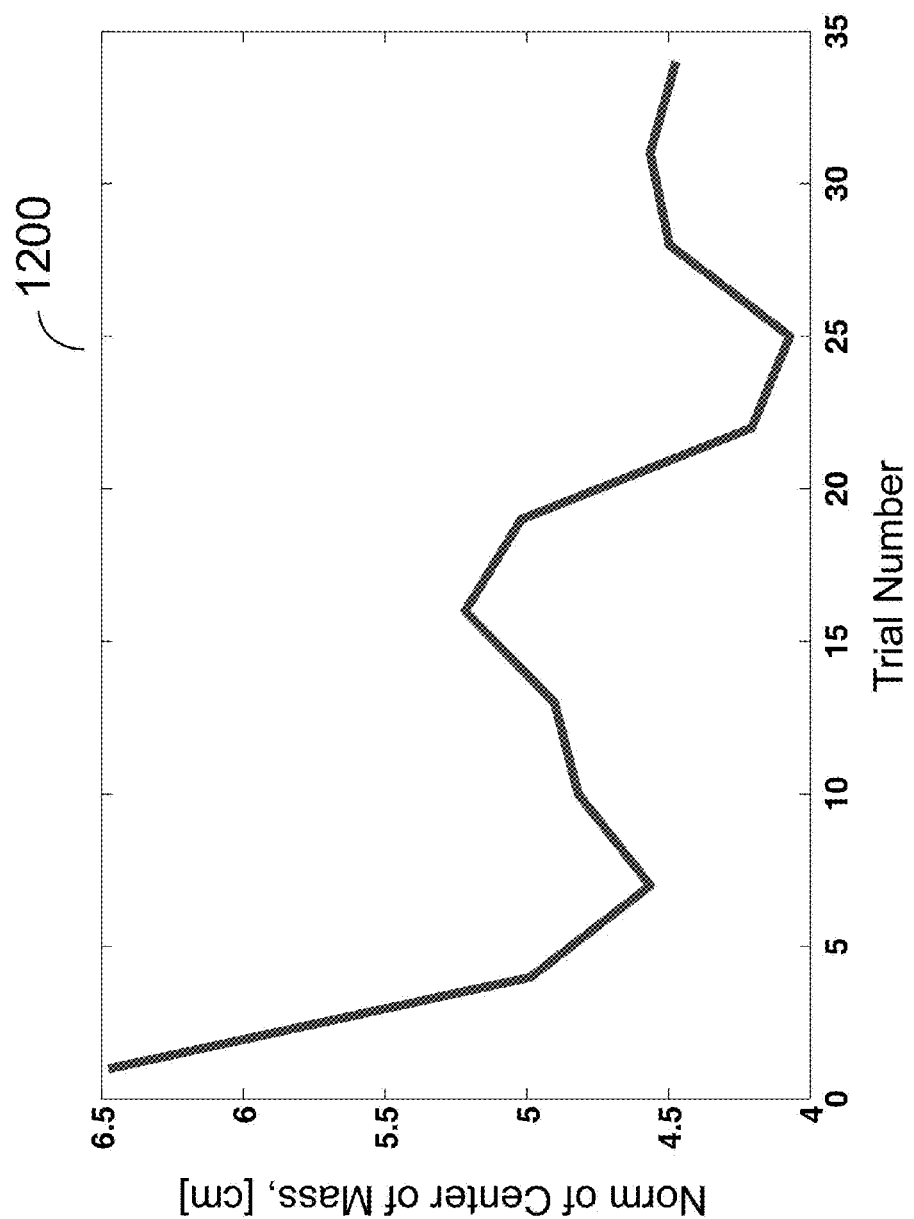
FIG. 12 is a graph depicting the norm of COM in the course of several example swing trials.

As an example, FIGS. 11A-11B show, respectively the "COM area" (ACOM) at 1) the instant when the arm has its maximum speed during the downswing phase (FIG. 11A); and 2) the time of initiating the downswing phase (FIG. 11B) for advanced golfers (bars 1102 and 1502 in depicted bar charts; handicap 9-14), intermediate golfers (bars 1104 and 1154 in depicted bar charts; handicap 14-20), and novice golfers (bars 1106 and 1156 in depicted bar charts; no handicap score). The figures show that the area of the COM at these two instants is significantly lower for advanced players and intermediate players than novice players. This suggests that advanced and intermediate players have better postural control during these two instants since they have a lower distance of COM with respect to the upright position, which is assumed to show perfect postural stability. FIG. 12 shows a typical example in which a player, using a visual feedback from the COM at the time of the maximum of arm speed during swing, improved his postural control after very few attempts (i.e., the norm of COM has been reduced). The norm of COM is defined in one embodiment as:

$$\text{norm}(COM) = (COM_{AP}^2 + COM_{ML}^2)^{0.5}$$

5.2. Non-Linearity

Returning to FIG. 10, the graph 1008 illustrates another metric that may be used to measure whether a particular swing is optimal. In one embodiment, this metric quantifies the non-linearity of the user's downswing curve. In particular, the non-linearity of the early downswing is used as a metric to determine optimal performance. This is based on the assumption that a flat and straight trajectory into impact achieves the best energy efficacy. This means that the COM moves on a linear trajectory from the top of backswing toward the address point. As a result, calculating the non-linearity of the downswing COM trajectory can provide an assessment of the quality of the swing, i.e., the more linear the downswing COM trajectory, the more optimal the swing.

In one embodiment, to estimate the non-linearity (1022), first the position of COM at address (1028) is projected in A-P direction onto the COM downswing curve, as shown by point 1020. Then, the maximum difference (1022) between the curve of the COM during the downswing phase and the straight line joining the top of the backswing (1024) and the projected point (1020) is calculated. In one embodiment, the estimated maximum distance between the straight line and the downswing curve is deemed to be the maximum non-linearity of the downswing curve. One embodiment normalizes this value by the range of motion of COM in A-P direction (1030) to estimate the percentage of non-linearity.

6. Computer System Embodiment

Figure 13:
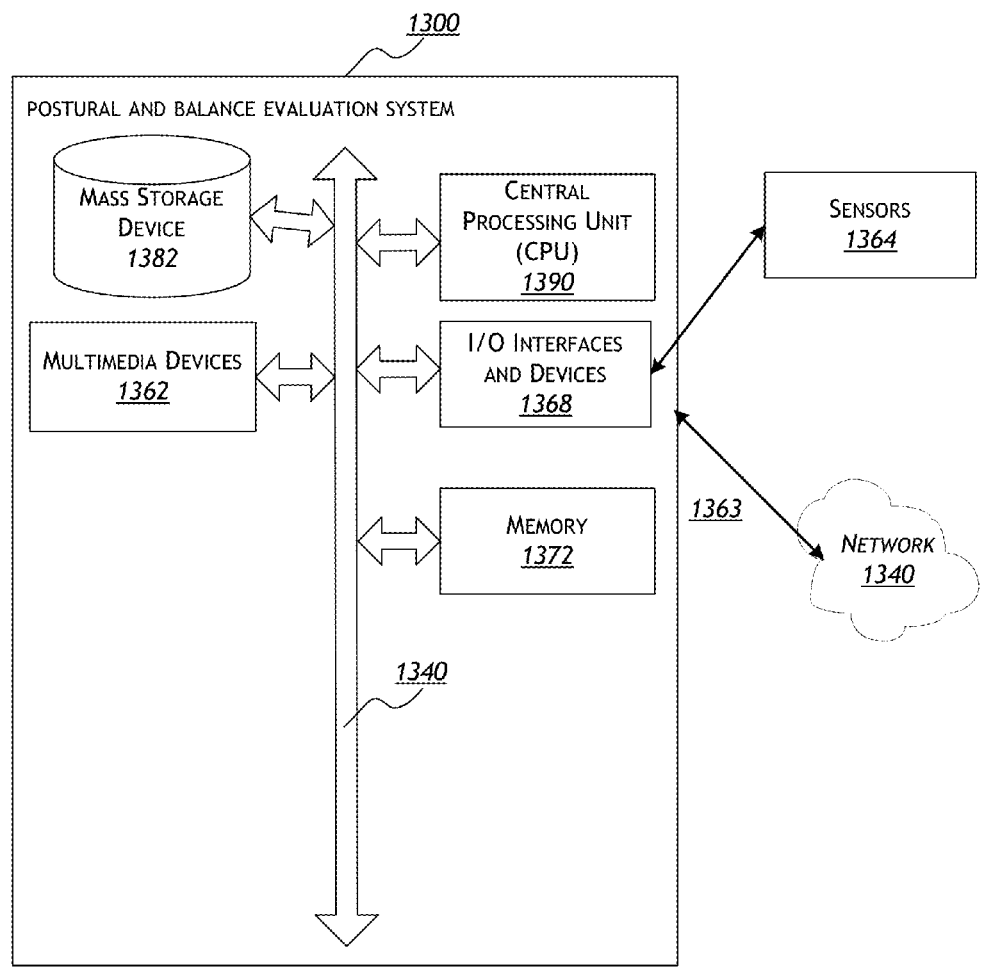
FIG. 13 is a block diagram illustrating the postural and balance evaluation system in accordance with one embodiment.

FIG. 13 is a block diagram illustrating the postural and balance evaluation system 1300 in accordance with one embodiment. The system 1300 may be implemented as a programmed computer system that comprises one or more computers or computing devices (e.g., application servers, database servers, workstations, storage servers, etc.) that execute code modules. The postural and balance evaluation system 1300 includes, for example, one or more personal computers that are IBM, Macintosh, or Linux/Unix compatible. In one embodiment, the postural and balance evaluation 1300 comprises one or more servers, desktop computers, laptop computers, personal digital assistants, kiosks, or mobile devices, for example. In one embodiment, the sample postural and balance evaluation system 1300 includes a central processing unit ("CPU") 1390, which may include one or more conventional microprocessors. The postural and balance evaluation system 1300 further includes a memory 1372, such as random access memory ("RAM") for temporary storage of information and a read only memory ("ROM") for permanent storage of information, and a mass storage device 1382, such as a hard drive, diskette, solid-state drive, or optical media storage device. The mass storage device 1382 may store data collected from a plurality of sensors or remotely collected sensor data, and/or calculated posture data from various trials. Typically, the components and modules of the postural and balance evaluation system 1300 are connected to the computer using a standard based bus system 1340. In different embodiments, the standard based bus system 1340 could be Peripheral Component Interconnect ("PCI"), Microchannel, Small Computer System Interface ("SCSI"), Industrial Standard Architecture ("ISA") and Extended ISA ("EISA") architectures, for example. In addition, the functionality provided for in the components and modules of postural and balance evaluation system 1300 may be combined into fewer components and modules or further separated into additional components and modules.

The postural and balance evaluation system 1300 is generally controlled and coordinated by operating system software, such as Windows Server, Linux Server, Windows XP, Windows Vista, Windows 7, Unix, Linux, SunOS, Solaris, Android, iOS, or other compatible server, desktop, or mobile operating systems. In Macintosh systems, the operating system may be any available operating system, such as MAC OS X. In other embodiments, the postural and balance evaluation system 1300 may be controlled by a proprietary operating system. Conventional operating systems control and schedule computer processes for execution, perform memory management, provide file system, networking, I/O services, and provide a user interface, such as a graphical user interface ("GUI"), among other things.

The sample postural and balance evaluation system 1300 may include one or more commonly available input/output (I/O) devices and interfaces 1368, such as a keyboard, mouse, touchpad, and printer. The I/O devices may also include the one or more sensors 1364 worn on a user's body, as described above. In one embodiment these devices may be linked physically to the system 1300, or may be linked wirelessly via interfaces such as Bluetooth. In one embodiment, the I/O devices and interfaces 1368 include one or more display device, such as a monitor, that allows the visual presentation of data to a user (e.g., the visual feedback user interface described above). More particularly, a display device provides for the presentation of GUIs, application software data, and multimedia presentations, for example. The postural and balance evaluation system 1300 may also include one or more multimedia devices 1362, such as speakers, video cards, graphics accelerators, and microphones, for example. In other embodiments, such as when the postural and balance evaluation system 1300 comprises a network server, for example, the computing system may not include any of the above-noted man-machine I/O devices.

In the embodiment of FIG. 13, the I/O devices and interfaces 1368 provide a communication interface to various external devices. For example, the postural and balance evaluation system 1300 is electronically coupled to the network 1340, which may comprise one or more of a LAN, WAN, or the Internet, for example, via a wired, wireless, or combination of wired and wireless, communication link 1363. The network 1340 facilitates communications among various computing devices and/or other electronic devices via wired or wireless communication links. The postural and balance evaluation system may use network 1340 to receive sensor data collected remotely and transmit such resulting data back to the user. For example, a user may wear sensors while he is playing at a golf course or driving range. The sensors may be configured to transmit data (through a wired or wireless connection) to a mobile computing device (e.g., a smartphone, a laptop computer, a tablet, etc.). The mobile communication device may in turn transmit the collected sensor data via the network 1340 to the postural and balance evaluation system 1300, which may, as described above, process the received data and provide feedback data back to the mobile computing device. The feedback data may then be used by the mobile computing device to display a visual feedback to the user (e.g., via a user interface described above). In this manner, the user can receive near-instantaneous feedback of his swings while he is at the golf course or driving range.

In addition to the devices that are illustrated in FIG. 13, the postural and balance evaluation system 1300 may communicate with other data sources or other computing devices. For example, collected data may be stored in a local or remote database by the postural and balance evaluation system 1300, so that a user's performance can be tracked over time.

The postural and balance evaluation system 1300 may also include one or more software modules to process perform the functionalities described herein, for example, the methods and processes depicted in FIGS. 3 and 14 and in Sections 3 and 4. The software module may be stored in mass storage 1382 or memory 1372, and implemented as one or more modules, which may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Alternately, the software module may be implemented as separate devices, such as computer servers. In alternate embodiments, the postural and balance evaluation system can be implemented by multiple physical computers that are interconnected, with different functions or tasks optionally handled by different machines.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

7. Conclusion

All of the methods and processes described above may be embodied in, and fully automated via, software code modules executed by one or more general purpose computers or processors. The code modules may be stored in any type of computer-readable medium or other computer storage device. Some or all of the methods may alternatively be embodied in specialized computer hardware. In addition, the components referred to herein may be implemented in hardware, software, firmware, or a combination thereof.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A method for providing data for use in displaying visual feedback for improving postural control and balance during a golf swing, comprising:

electronically receiving with one or more computing devices data collected from one or more sensors worn on a body of a person;

determining, with the one or more computing devices, one or more center of mass positions of the person based on the data collected from the one or more sensors, the data reflecting movement and position of the person while performing a golf swing;

generating first visual display data corresponding to a first visual indication reflecting said one or more determined center of mass positions;

generating second visual display data corresponding to a second visual indication reflecting a target center of mass position for the person that has been determined to contribute to a desired performance of the golf swing; and providing the first and second visual display data for use in displaying the first and second visual indications to the person, wherein the first and second visual indications enable the person to determine a difference between (1) at least said one or more center of mass positions of the person while performing the golf swing reflected by the first visual indication and (2) the target center of mass position reflected by the second visual indication, such that the person can improve golf swing performance by reducing said difference, and wherein said one or more sensors comprise at least one of: an accelerometer, gyroscope, and magnetometer.

2. The method of claim 1, wherein said target center of mass position that has been determined to contribute to the desired performance of the golf swing is determined based on data collected from the sensors when the person is in a standing position and not performing the golf swing.

3. The method of claim 1, wherein said determining one or more center of mass positions comprises:

segmenting the golf swing into a plurality of temporal phases;

wherein said determining, with the one or more computing devices, comprises calculating, for each temporal phase, an associated center of mass position of said one or more determined center of mass positions and wherein the first visual indication further reflects the associated center of mass position for each temporal phase to be compared with the target center of mass position that has been determined to contribute to the desired performance of the golf swing.

4. The method of claim 3, wherein the temporal phases comprise one or more of: a back swing portion of the golf swing, a down swing portion of the golf swing, a top of the back swing, a time of contact with the ball, and a time at which an arm of the person has reached its maximum speed.

5. The method of claim 4, wherein said one or more sensors includes a sensor worn on the arm of the person and said temporal phases are determined based at least in part on data collected from said sensor worn on the arm.

6. The method of claim 3, wherein the temporal phases comprise user-specified temporal phases.

7. The method of claim 1, wherein said determining one or more center of mass positions is based on a single-link model.

8. The method of claim 1, wherein said determining one or more center of mass positions is based on a multiple-link model.

9. The method of claim 1, further comprising:
determining a non-linearity of the golf swing based on said one or more determined center of mass positions.

10. The method of claim 1, further comprising:
determining a deviation between one of said one or more determined center of mass positions and the target center of mass position that has been determined to contribute to the desired performance of the golf swing; and normalizing said deviation by a maximum speed of an arm of the person during the golf swing.

11. A system for providing data for use in displaying visual feedback for improving postural control and balance during a golf swing, the system comprising:

a computing system configured to receive sensor data from one or more sensors worn on a body of a person, the data reflecting movement and position of the person while performing a golf swing;

wherein the computing system is further configured to:
determine one or more center of mass positions of the person based on the data collected from said one or more sensors;

generate visual display data corresponding to a visual feedback on the golf swing, the visual feedback reflecting a difference between said one or more determined center of mass positions and a target center of mass position for the person that has been determined to contribute to the desired performance of the golf swing; and provide the visual display data for use in displaying the visual feedback to the person, wherein said one or more sensors comprise at least one of: an accelerometer, gyroscope, and magnetometer.

12. The system of claim 11, wherein said target center of mass position that has been determined to contribute to the desired performance of the golf swing is determined based on data collected from said one or more sensors when the person is in a standing position and not engaged in the golf swing.

13. The system of claim 11, wherein said computing system is configured to determine said one or more center of mass positions by at least:

segmenting the golf swing into a plurality of temporal phases; and for each temporal phase, identifying an associated center of mass position of said one or more center of mass positions.

14. The system of claim 13, wherein the temporal phases comprise one or more of: a back swing portion of the golf swing, a down swing portion of the golf swing, a top of the back swing, a time of contact with the ball, and a time at which an arm of the person has reached its maximum speed.

15. The system of claim 14, wherein said one or more sensors includes a sensor worn on the arm of the person and said temporal phases are determined based at least in part on data collected from said sensor worn on the arm.

16. The system of claim 14, wherein said one or more sensors includes a sensor worn on the arm of the person and wherein speed of the arm is determined based at least in part on the data collected from said sensor worn on the arm.

17. The system of claim 11, wherein said computing system is electrically connected to said one or more sensors.

18. The system of claim 11, wherein said computing system is configured to receive the data collected from said one or more sensors wirelessly.

19. The system of claim 11, wherein said data collected from said one or more sensors is transmitted via a network to said computing system.

20. The system of claim 11, wherein said one or more sensors comprise sensors embedded in a mobile device carried by the person.

21. The system of claim 11, wherein said computing system is further configured to determine a non-linearity of the golf swing based on said one or more determined center of mass positions.

22. The system of claim 11, wherein said computing system is further configured to:
- determine a deviation between one of said one or more determined center of mass positions and the target center of mass position that has been determined to contribute to the desired performance of the golf swing; and
- normalize said deviation by a maximum speed of an arm of the person during the golf swing.

23. A method for providing data for use in presenting feedback for improving postural control and balance of a person engaged in a sport activity, the method comprising:
- electronically receiving with one or more computing devices data collected from one or more sensors worn on a body of a person engaging in a sport activity;
- determining, with the one or more computing devices, one or more center of mass positions of the person based on the data collected from the one or more sensors, the data reflecting movement and position of the person while performing the sport activity;
- generating feedback data corresponding to feedback indicating a difference between said one or more determined center of mass positions and a target center of mass position determined based on sensor data received when the person is in a pre-defined position; and
- providing the feedback data for use in presenting the feedback,
- wherein said one or more sensors comprise at least one of: an accelerometer, gyroscope, and magnetometer.

24. The method of claim 23, wherein said pre-defined position is specified by a user input.

25. The method of claim 23, wherein said pre-defined position is a standing position and the person is not engaged in the sport activity.

26. The method of claim 23, wherein one of said one or more determined center of mass positions is determined when an arm of the person has reached maximum speed during the sport activity.

27. Non-transitory computer storage that stores executable code that directs a computing system to at least:
- electronically receive by the computing system data collected from one or more sensors worn on a body of a person engaging in a sport activity;
- determine, with the computing system, one or more center of mass positions of the person based on the data collected from the one or more sensors, the data reflecting movement and position of the person while performing the sport activity;
- determine, with the computing system, a target center of mass position based on sensor data received when the person is in a standing position and not engaged in the sport activity;
- generate indication data corresponding to an indication of a difference between said one or more determined center of mass positions and the target center of mass position; and
- provide the indication data for use in presenting the indication, wherein said one or more sensors comprise at least one of: an accelerometer, gyroscope, and magnetometer.

* * * * *

UNITED STATES PATENT AND TRADEMARK OFFICE
CERTIFICATE OF CORRECTION

PATENT NO. : 8,979,665 B1
APPLICATION NO. : 13/053147
DATED : March 17, 2015
INVENTOR(S) : Bijan Najafi et al.

It is certified that error appears in the above-identified patent and that said Letters Patent is hereby corrected as shown below:

In the specification,

In column 7 at line 41, Change "offsetEadded" to --offset □ added--

In column 9 at line 3, Change "$\vec{COM} - K_1 \cdot \sin \theta_a, aK_2 \cdot \sin \theta_i$" to --$\vec{COM} = K_1 \cdot \sin\theta_a + K_2 \cdot \sin\theta_k + K_3 \cdot \sin\theta_t$--.

In column 9 at line 19, Change "$\vec{COM}\ K_1 \cdot \sin \theta_a, aK_2 \cdot \sin \theta_i$" to --$\vec{COM} = K_1 \cdot \sin\theta_a + K_2 \cdot \sin\theta_t$--.

Signed and Sealed this
Twenty-ninth Day of March, 2016

Michelle K. Lee
*Director of the United States Patent and Trademark Office*